US00PP09854P

United States Patent [19]

Dümmen

[11] Patent Number: Plant 9,854

[45] Date of Patent: Apr. 8, 1997

[54] POINSETTIA PLANT NAMED HWD SPOTLIGHT

[75] Inventor: Günter Dümmen, Rheinberg-Eversael, Germany

[73] Assignee: Dummen Jungpflanzenkulturen, Rheinberg Eversael, Germany

[21] Appl. No.: 516,463

[22] Filed: Aug. 17, 1995

[51] Int. Cl.[6] ..... A01H 5/00

[52] U.S. Cl. ..... Plt./86.4

[58] Field of Search ..... Plt./86.4

*Primary Examiner*—James R. Feyrer

*Attorney, Agent, or Firm*—Proprietary Rights International

[57] ABSTRACT

A new and distinct cultivar of Poinsettia plant named HWD Spotlight, characterized by its dark red flower bracts; dark green leaves; entire, usually note lobed, flower bracts; freely branching plant habit; and excellent postproduction longevity.

1 Drawing Sheet

The present invention relates to a new and distinct cultivar of Poinsettia plant, botanically known as *Euphorbia pulcherrima* Willd., known as the variety Duespot, and hereinafter referred to by the cultivar name HWD Spotlight.

The new cultivar is a product of a planned breeding program conducted by the inventor in Rheinberg, Germany.

The new cultivar originated from a cross made by the inventor of the cultivar Angelika (U.S. Pat. No. P.P. 5,492) as the male or pollen parent with the cultivar Red Sails (U.S. Pat. No. P.P. 6,980) as the female or seed parent.

The cultivar HWD Spotlight was discovered and selected by the inventor as a flowering plant within the progeny of the stated cross in a controlled environment in Rheinberg, Germany. Asexual reproduction of the new cultivar by terminal cuttings taken at Rheinberg, Germany, has shown that the unique features of this new Poinsettia are stabilized and reproduced true to type in successive generations of asexual reproduction.

The following traits have been repeatedly observed and are determined to be the unique characteristics of HWD Spotlight. These characteristics in combination distinguish HWD Spotlight as a new and distinct cultivar:

1. Dark red flower bracts.
2. Dark green leaves.
3. Entire flower bracts, usually not lobed.
4. Freely branching plant habit.
5. Excellent postproduction longevity.

In comparison to the parent cultivar Angelika, the new Poinsettia has darker leaf color; darker flower bract color; and longer postproduction longevity as flower bract color does not fade as quickly. In comparison to the parent cultivar Red Sails, the new Poinsettia has entire, usually not lobed, flower bracts; is more freely branching; and has longer postproduction longevity as the leaves are retained longer.

The accompanying colored photograph illustrates the overall appearance of the new cultivar, showing the colors as true as it is reasonably possible to obtain in colored reproductions of this type. The photograph comprises a top perspective view of a typical potted plant of HWD Spotlight with one pinched plant in a 15-cm container.

The cultivar HWD Spotlight has not been observed under all possible environmental conditions. The phenotype may vary somewhat with variations in environment such as temperature, daylength and light intensity, without, however, any variance in genotype. The following observations, measurements and comparisons describe plant grown in Rheinberg, Germany, under commercial practice in a glass-covered greenhouse with day temperatures of 22° C. and night temperatures of 18° C. and light levels of 30,000 to 40,000 lux. Plants were grown in 15-cm pots with one pinched plant per pot.

In the following description, color references are made to The Royal Horticultural Society Colour Chart except where general terms of ordinary dictionary significance are used.

Classification:

*Botanical.*—*Euphorbia pulcherrima* Willd.

*Commercial.*—Poinsettia.

*Cultivar.*—'HWD Spotlight'.

Parentage:

*Male parent.*—'Angellika' (U.S. Pat. No. P.P. 5,492).

*Female parent.*—'Red Sails' (U.S. Pat. No. P.P. 6,980).

Propagation:

*Type cutting.*—Terminal cuttings.

*Time to initiate roots.*—Summer: 27° C., 21 days; winter: 20° C., 28 days.

*Rooting habit.*—Fine, freely branching.

Plant description:

*Plant form.*—Vase-shaped.

*Growth habit.*—Freely branching and upright. Branching is enhanced by the removal of the apical shoot tip.

Foliage description:

*Arrangement.*—Opposite.

*Size.*—Length: 11 to 12 cm. Width: 9 to 10 cm.

*Shape.*—Ovate.

*Tip.*—Acuminate.

*Base.*—Acute.

*Margin.*—Lobed.

*Texture.*—Upper side: Glabrous. Under side: Pubescent at veins.

*Color.*—Young foliage upper side: Much darker than 147A. Young foliage under side: 147A. Mature foliage top side: Much darker than 147A. Mature foliage under side: 147A.

*Venation.*—Pattern: Pinnate. Upper side: 147B. Under side: Center vein, 183A; lateral veins, 147B.

*Petiole.*—Length: 5 to 6 cm. Color: 183A.

Flower description:

*Inflorescence type and habit.*—Inflorescences are compounds corymbs of cyathia with colored bracts subtending the cyathia.

*Natural flowering season.*—Autumn/winter in Northern Hemisphere. Flower initiation and development can be induced under short day/long night conditions.

*Time to flower.*—8.5 weeks under short day/long night conditions.

*Quantity of inflorescence.*—8 to 12 cyathia per corymb.

*Inflorescence size.*—Diameter: 29 cm. Height (depth): 6 cm.

*Flower bracts.*—Attitude: Horizontal to stem axis. Quantity of flower bracts: 17 per inflorescence. Size: Length: 13 to 14 cm. Width: 7.5 cm. Shape: Ovate. Tip: Acuminate. Base: Acute. Margin: Entire, usually not lobed. Texture: Upper side: Satiny, glabrous. Under side: Smooth, glabrous Color: When opening: 185A. Mature, top side: Slightly lighter than 46A. Mature, under side: 45A. Fading to: Flower bract color does not fade. Venation: Upper side: 187B. Under side: 183C. Petiole: Length: 14 to 16 cm. Color: 146B, slight hint of 183A.

*Cyathia.*—Quantity: 8 to 12 per cyathium. Color: Immature: 144C. Mature: 144A. Diameter of cyathia cluster: 2.5 to 3 cm. Stamens: Stamen number: 10 to 15 per cyathia Anther size: 0.5 mm. Anther color: 185A. Pollen color: 11A. Pistils: Pistil number: 1 per cyathium. Stigma color: 187A/187B. Style color: 144A at base, 187B/187C at stigma. Style length: 2 mm. Ovary number: 3. Nectaries: Usually one and sometimes two per cyathium.

Disease resistance: No fungal, bacterial nor viral problems observed.

Postproduction longevity: Generally more than 5 weeks under interior conditions.

It is claimed:

1. A new and distinct cultivar of Poinsettia plant named HWD Spotlight, as illustrated and described.

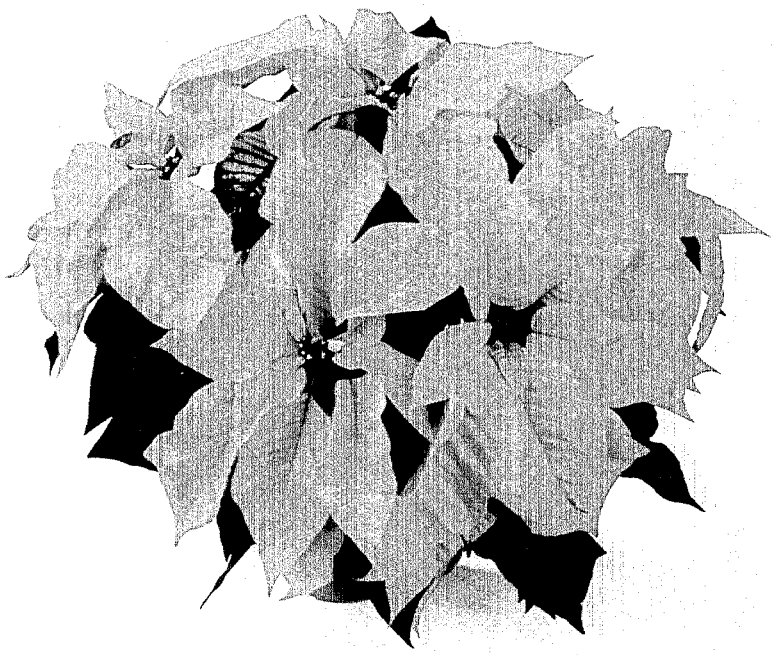

* * * * *